(12) United States Patent
Zhu et al.

(10) Patent No.: US 7,875,729 B2
(45) Date of Patent: Jan. 25, 2011

(54) PROCESS FOR MAKING ASENAPINE

(75) Inventors: Jie Zhu, Nijmegen (NL); Rolf Keltjens, Wijchen (NL); Judith Firet, Ede (NL)

(73) Assignee: Synthon BV, Nijmegen (NL)

( * ) Notice: Subject to any disclaimer, the term of this patent is extended or adjusted under 35 U.S.C. 154(b) by 425 days.

(21) Appl. No.: 12/004,925

(22) Filed: Dec. 21, 2007

(65) Prior Publication Data
US 2008/0214832 A1 Sep. 4, 2008

Related U.S. Application Data

(60) Provisional application No. 60/883,603, filed on Jan. 5, 2007.

(51) Int. Cl.
*C07D 491/044* (2006.01)
*C07D 313/14* (2006.01)
(52) U.S. Cl. ...................... 548/421; 549/354
(58) Field of Classification Search ................ 548/421; 549/354
See application file for complete search history.

(56) References Cited

U.S. PATENT DOCUMENTS 4,145,434 A 3/1979 van der Burg

FOREIGN PATENT DOCUMENTS

| EP | 1 710 241 A1 | 10/2006 |
|---|---|---|
| WO | WO 95/23600 | 9/1995 |
| WO | WO 99/32108 | 7/1999 |

OTHER PUBLICATIONS

Th. de Boer et al., "Antipsychotic Dopamine D2 Receptor Antagonist 5-HT2 Receptor Antagonist" Drugs of the Future 1993, 18(12): 1117-1123.
C. W. Funke et al., "Physico-chemical Properties and Stability of trans-5-Chloro-2-methyl-2,3,3a,12b-tetra . . . " Arzneim-Forsch/Drug Res., 40(1) Nr. 5 (1990) pp. 536-539.

*Primary Examiner*—Joseph R Kosack
(74) *Attorney, Agent, or Firm*—Muncy, Geissler, Olds & Lowe, PLLC

(57) ABSTRACT

Asenapine and related trans-isomer bicyclic compounds can be obtained by reducing a compound of formula (C) to preferentially form a trans-isomer compound of formula (D), followed by subsequent ring closure to form a compound of formula (B) such as asenapine.

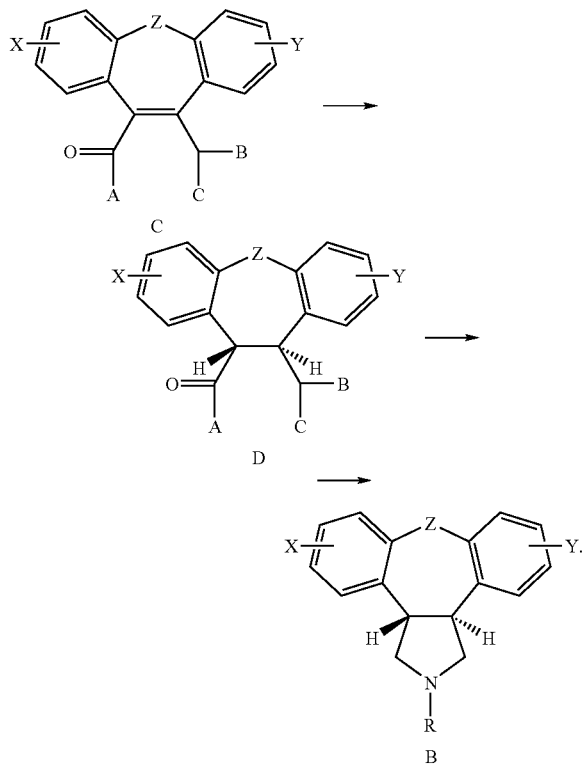

22 Claims, No Drawings

PROCESS FOR MAKING ASENAPINE

This application claims the benefit of priority under 35 U.S.C. §119(e) from U.S. Provisional Application Ser. No. 60/883,603, filed Jan. 5, 2007, the entire contents of which are incorporated herein by reference.

BACKGROUND OF THE INVENTION

The present invention relates to processes and intermediates useful in the production of asenapine and related compounds.

Asenapine, trans-5-chloro-2-methyl-2,3,3a,12b-tetrahydro-1H-dibenz[2,3:6,7]oxepino[4,5-c]pyrrole of the formula (1)

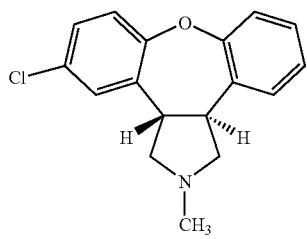

is a compound having CNS-depressant activity (see Boer et al, Drugs of the Future, 18(12), 1117-1123, 1993) and may be used in the treatment of depression (WO 99/32108). The compound corresponding to the above formula is a trans-racemate. Both enantiomers within this racemate contribute equally to the clinical effect of asenapine. In pharmaceutical compositions, particularly intended for sublingual and buccal administration, the asenapine as defined above may be advantageously used as the maleate salt (WO 95/23600). Physicochemical properties of the drug substance have been reported by Funke et al. (Arzneim.-Forsch/Drug Res., 40,536-539, 1990).

Asenapine is a specific example from a class of pharmaceutically active compounds,

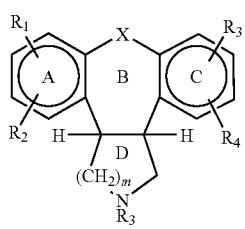

that was disclosed in U.S. Pat. No. 4,145,434. General methodology for the preparation of asenapine is also described therein.

The synthetic approach derivable from the teaching of U.S. Pat. No. 4,145,434 and disclosed in full in Example 9 of EP 1710241 is shown in the following scheme.

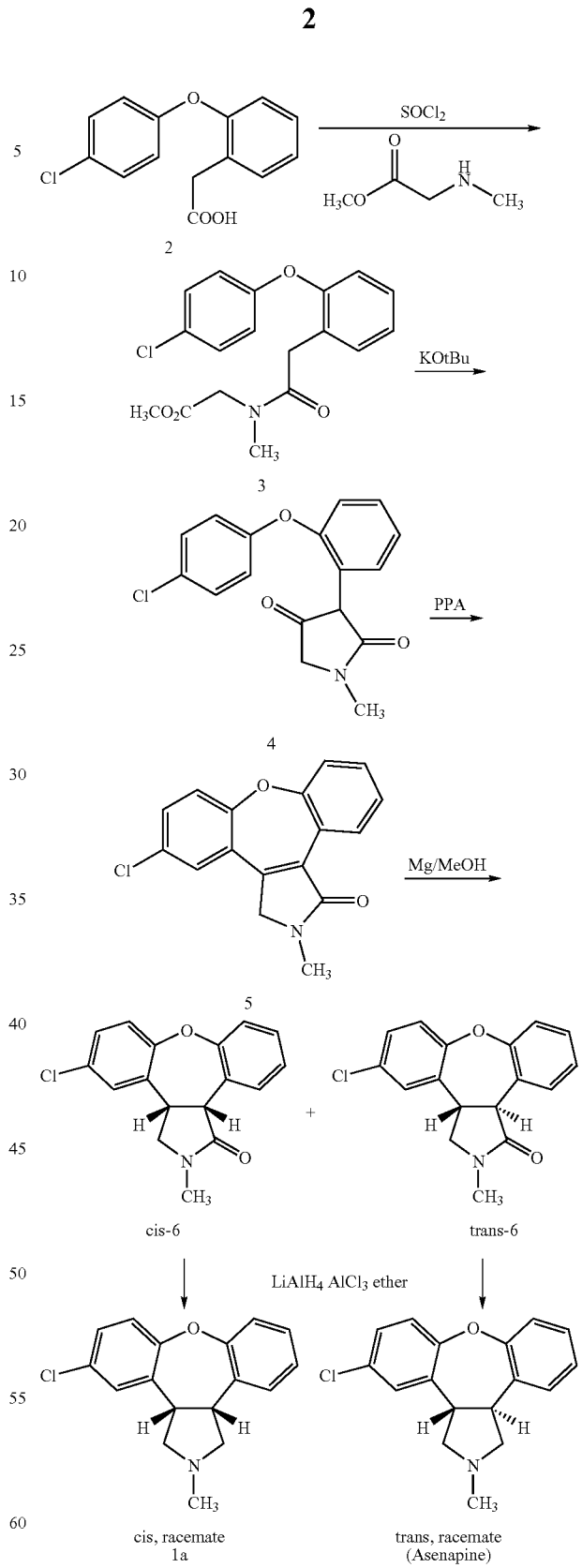

For preparing Asenapine from the acid (2), the carboxyl group is first transformed into the corresponding acid chloride by treatment with thionylchloride. Coupling with sarcosinemethyl ester provides for an ester (3). Treatment of the ester (3) with potassium tert-butoxide in toluene yields the cyclic dione (4), which is subjected to further ring closure to an enamide (5) by treatment with polyphosphoric acid.

The step of reducing the enamide (5) with magnesium in methanol gave a mixture of cis and trans lactam (6). Both isomers must be separated by column chromatography. It appears that the formation of the cis-lactam (6) is predominant (approx. 4:1 cis/trans). After separation, reduction of the cis or trans lactam (6) with LiAlH$_4$/AlCl$_3$ finally furnished the cis amine (1a) or desired trans amine (Asenapine), respectively. Because the cis isomer is predominant, the synthesis is not optimal.

An alternative synthetic route proceeds via the compound (6a),

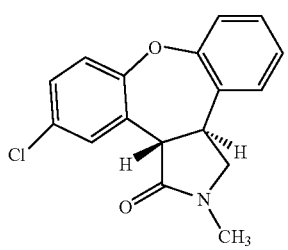

6a which is the regio-isomer of the compound (6) and which may be reduced to asenapine similarly as the compound (6). A suitable way for making (6a) may be similar to the process of making (6), i.e. is based on the reduction of the enamide (5a)

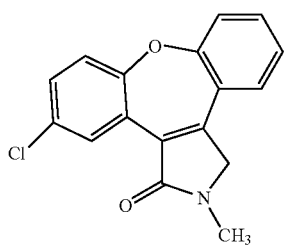

5a which, in turn, may be prepared in an analogous process as disclosed above, starting with the corresponding regioisomer of the compound (2); namely the compound (2a)

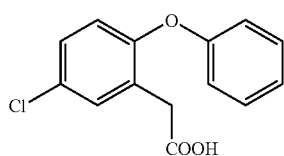

2a (see Vader et al., J. Labelled Comp., Radiopharm., 34, 845-869, 1994). Similarly as the conversion of (5) to (6), the conversion of (5a) to (6a) yields predominantly the undesired cis-isomer.

An alternate way of making the compound (6a) has been described in Example 8 of the EP 1710241 (US 2006/0229352, WO 2006/106136)

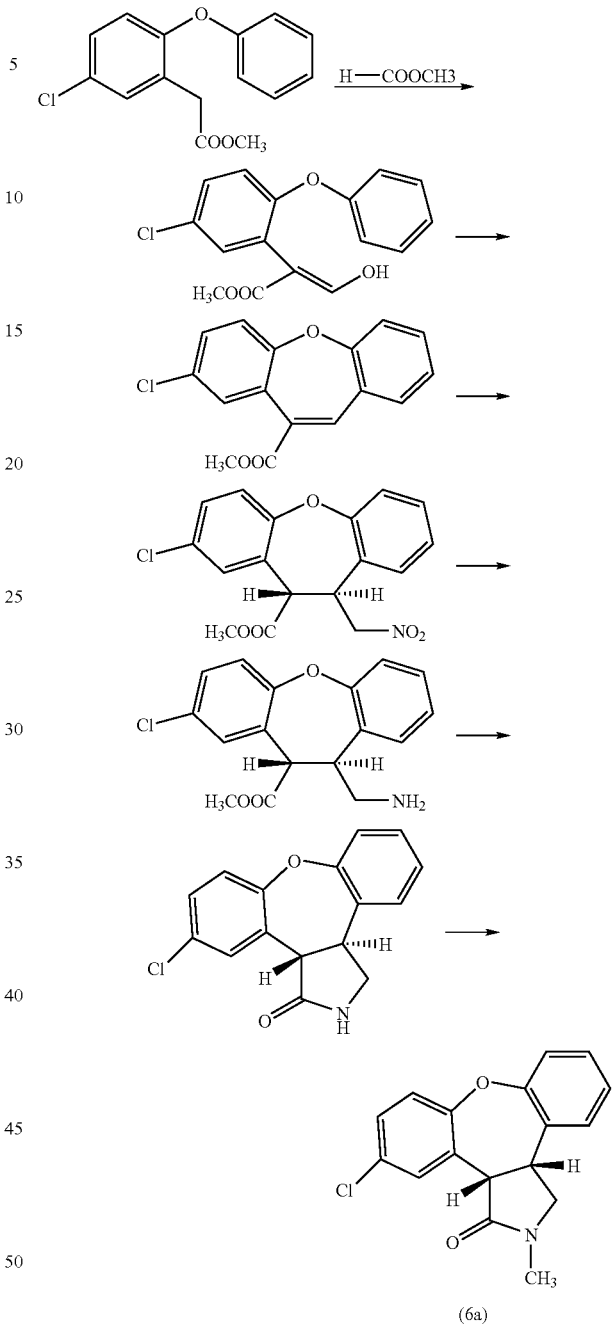

(6a)

It seems from the disclosure that this reaction exhibits good yields, but it also predominantly provides the unwanted cis-isomer of the compound (6a) upon subsequent work up, which leads consequently to the cis-asenapine (1a).

According to EP '241, the unfavourable product ratio may be improved by subsequent partial isomerization of the unwanted cis-isomer of the lactam (6) or (6a) into the trans-lactam using 1,5-diazabicyclo[4,3,0]non-5-ene (DBN), yielding an trans-cis equilibrium in approx. 1:2 ratio. Repeated isomerization may provide an overall 38% yield of the trans-(6) isomer, starting from the enamide (5).

The formation of the desired trans-isomer of the amide (6) or (6a) in low relative amounts is a serious disadvantage in the above-mentioned asenapine processes. Its amount may be enhanced by a partial racemization as indicated above. But the cis-amide apparently is thermodynamically more stable isomer than the trans-amide, so that a racemization as a possible way how to enhance the yield of the desired trans-amide (6) is not a particularly effective solution. Another problem arises with the separation of the trans amide from the cis amide. Even by using of column chromatography, a pure trans-isomer is difficult to be obtained.

An attempt to solve the problem was disclosed in EP 1710241. The cis-trans mixture of the compound (6) and/or its regio-isomer (6a), preferably without separating the enantiomers, undergoes the ring-opening reaction by an excess of strong base in an alcoholic medium, wherein it was found that predominantly a trans-isomer of the amino/ester of the formula (7) and/or of the formula (7a) may be formed

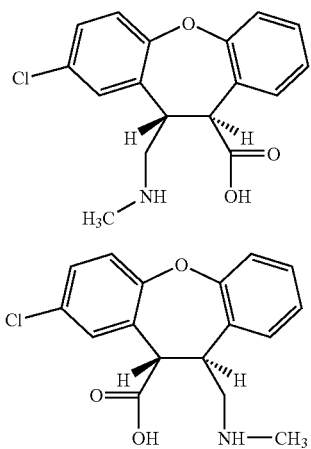

in an approx. ratio 10:1 (trans: cis). The trans-(7) or the trans-(7a) may be isolated and subjected to re-cyclization yielding the desired trans-(6) or trans-(6a) with the overall yield of about 60% in respect to the compound (5). More advantageously, the trans-compound (7) or (7a) may be converted to asenapine directly, by a cyclization by treating with a reducing agent, optionally with a combination with a Lewis acid.

It would be desirable to find an alternative route to make asenapine and/or trans intermediates thereof in good isomeric purity. It would also be desirable to have a process that could be applied to making other related trans-configuration compounds such as those described in U.S. Pat. No. 4,145,434.

SUMMARY OF THE INVENTION

The present invention relates to the discovery that trans selective reduction can be readily adapted to making asenapine and related pharmaceuticals and their intermediates. Accordingly, a first aspect of the present invention relates to a process, which comprises reducing a compound of formula (C) to preferentially form a trans isomer compound of formula (D)

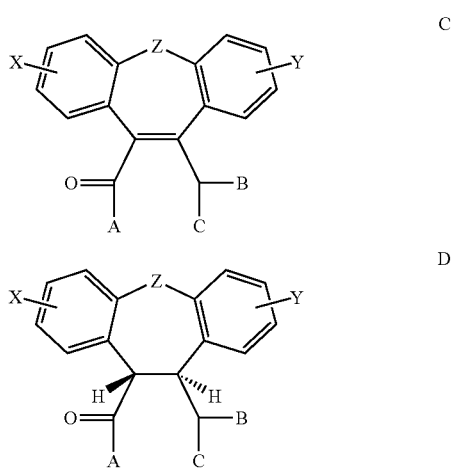

wherein Z represents an oxygen, sulfur, or methylene linkage group; X and Y independently represent hydrogen, an alkyl group, a hydroxy group, an alkoxy group, a halo group, a nitro group, an amino group, a substituted amino group, a cyano group, a sulfonyl group, a carboxyl group, a substituted carboxy group and combinations thereof, and wherein X and Y can each be present up to four times on their respective rings and each occurrence is independently selected; and A represents a group of the formula O—R1; B represents hydrogen or a =O group; and C represents an amino group, a methylamino group or a group of the formula O—R2; wherein R1 and R2 are each individually selected from hydrogen, alkyl, alkynyl and aralkyl groups.

Preferably, Z is oxygen and R1 and R2 are a C1-C4 alkyl group, most preferably a methyl group. The reduction preferentially forms the trans isomer compound of formula (D), meaning that more of the trans isomer configuration is produced than the cis configuration by the reduction. Typically the preference is at least 60:40 (trans:cis) and is generally much higher.

The trans compound of formula (D) can be converted to a compound of formula B by ring closing

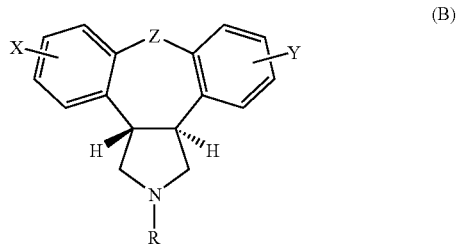

wherein R represents an alkyl or an aralkyl group.

In a specific aspect, the general formula (B) is represented by the compound of formula (1), the general formula (C) is represented by the compound of formula (8) and the general formula (D) is represented by the compound of general formula (9).

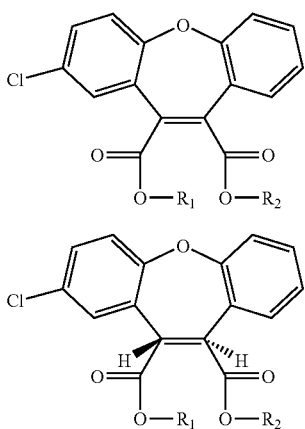

In a more specific aspect, the conversion of the compound (8) to asenapine of formula (1) proceeds according to the following scheme:

DETAILED DESCRIPTION OF THE INVENTION

Throughout this disclosure, compounds represented by structural formulae having a pair of bold and hashed wedged bonds, as shown, e.g., in compound (1) above, shall refer to "trans" diastereomers. Formulae with a pair of bold wedged bonds shall refer to "cis" diastereomers. Each of the compounds may exist as a single enantiomer having the absolute stereochemical configuration indicated by the wedged bonds or having the opposite absolute configuration, or each of the compounds may exist as a mixture of enantiomers (e.g. as a racemate) having the relative stereochemical configuration indicated by the wedged bonds. Additionally, the term "alkyl" includes 1-6 carbon atoms, typically 1-4; the term alkynyl includes 2-6 carbon atoms, typically 2-4; the term aralkyl includes 7 to 10 carbon atoms; and the term aryl includes 6 to 7 carbon atoms such as a tosyl moiety.

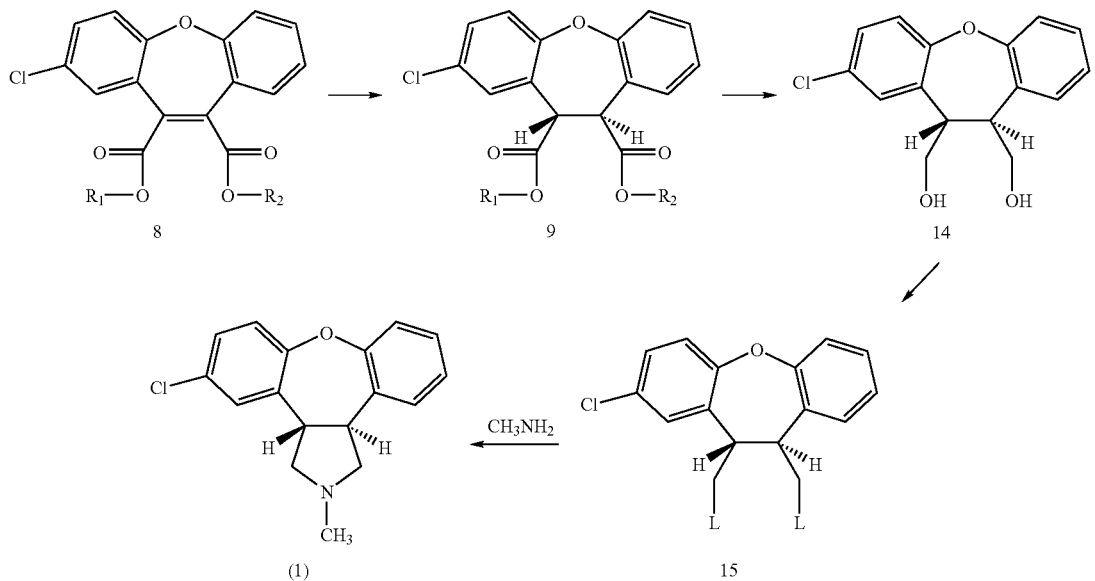

The invention further provides for a convenient process for making the compound of formula (8), which may be applied as a general process for making the compounds of general formula (B).

Within the above process, the compound (1) may be obtained having the trans-cis ratio in the product comprising the compound higher than 80:20, preferably higher than 90:10 and most preferably higher than 95:5

The compounds of formulae (8), (9), (14) and (15), particularly the trans-compounds (9), (14) and (15) with higher than 80% isomeric purity, represent a specific aspect of the invention.

A common synthetic issue in forming asenapine and structurally similar compounds is the formation of the fused seven- and five-membered ring structure (A) in the desired configuration;

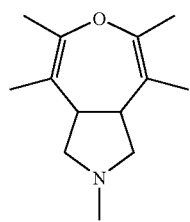

A e.g., how to obtain the desired trans-configuration on the C—C bond bridging the two rings. Such bicyclic structure appears in the amide compound (6) and/or (6a) and the trans-isomer thereof is generally obtainable in low amounts, relative to the formation of the corresponding cis-isomer.

The present inventors considered that an advantageous approach to reach predominant trans-isomer configuration of the above ring-structure (A) would involve leaving one of the rings (five or seven member ring) open until the desired configuration is reached and then closing the ring. Thus the invention includes leaving the future five-membered ring open, and to proceed via a compound comprising a ring structure of a general formula (A-1)

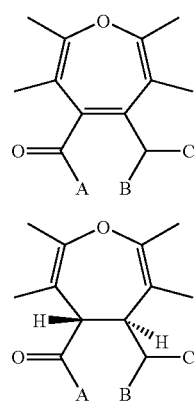

A-1

A-2 group, a hydroxy group, an alkoxy group, a halo group, a nitro group, an amino group, an substituted amino group, a cyano group, a sulfonyl group, a carboxyl group, a substituted carboxy group etc., and combination thereof, Z may be methylene, oxygen or sulfur bridge and R may be an alkyl or an aralkyl group; among which the asenapine of formula (1) is a specific example.

According to the above approach, the compound of general formula (B) may be prepared from a compound of general formula (C) via a trans-reduction of a C—C double bond to a compound of general formula (D),

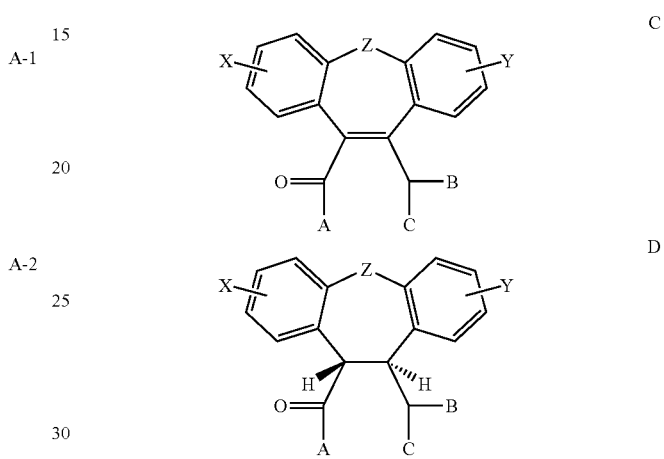

C

D wherein A, B and C are functional groups that may be converted, directly or stepwise, into a tetrahydropyrrole ring present in the structure (A). In particular, the existence of at least one carbonyl group conjugated with a C—C double bond is the characteristic feature of the ring structure (A-1) and, from thermodynamic and kinetic aspects, the presence thereof is thought to aide the selective trans-reduction of the C—C double bond. After such a trans-reduction is achieved and a ring-structure of general formula (A-2) is obtained, then the tetrahydropyrrole ring may be constructed with the retention of the trans-configuration. Moreover, whenever the reduction of the so conjugated C—C double bond would yield a substantial amount of the cis-isomer, such cis-isomer can be racemised by a base-catalysed process and this may enhance the overall yield of the trans-product.

In theory, leaving the seven member ring open and working according to the above principle should have a similar effect.

In general, the above approach may be applied to a synthesis of any compound of the general formula (B)

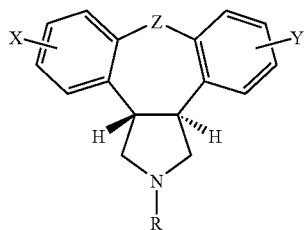

B wherein X and Y may independently be one to four hydrogens or furthers substituents selected preferably from an alkyl followed by converting the compound of general formula (D) into a compound of general formula (B).

In the above formulae (C) and (D), the X, Y, and Z have the same meaning as for the above compound of general formula (B) and A, B and C are functional groups that may be converted, directly or stepwise, upon formation a tetrahydropyrrole ring. More specifically, the functional group B is hydrogen or the =O group, the functional group A is a group of the general formula O—R1 and the functional group C is an amino group, a methylamino group or a group of a general formula O—R2, wherein R1, R2 is either hydrogen or the same or different alkyl, alkynyl or aralkyl group, preferably R1 and R2 are the same C1-C4 alkyl group and most preferably are a methyl group.

The invention will be further illustrated on the process for making asenapine of formula (1) and pharmaceutically acceptable salts thereof and it is obvious that it may be extended to derivatives thereof within the structure of the general formula (B).

The preferred starting compound within each of the general formulae (C) and (D) is the diester compound of the formula (8) and (9), respectively.

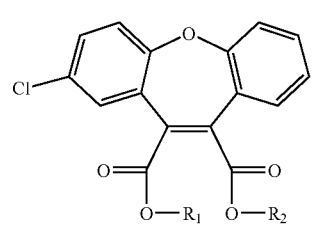

8

-continued

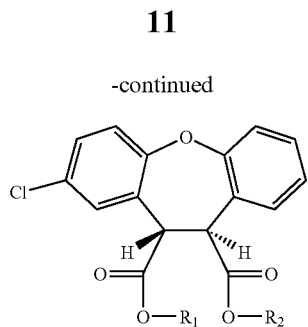

9

In the above structures, R1 and R2 are the same or different alkyl, alkynyl or aralkyl group, preferably R1 and R2 are the same C1-C4 alkyl group and most preferably are a methyl group. Surprisingly the reduction of compound (8) preferentially yields the trans configuration shown in compound (9). Thus typically conventional reduction steps/techniques can be used, e.g., using a reductant such as magnesium in alcohol, hydrogen with a hydrogenation catalyst, a hydride reductant, etc., to achieve selective trans-configuration formation.

As used herein selective or preferential trans reduction means that more of the trans configuration is formed than the cis by the reduction step. Typically the ratio is at least 60:40, more typically at least 70:30, often at least 80:20 and even 90:10 or 95:5 (trans:cis). Accordingly, reducing the double bond in a compound of formula (8) or more generally (C), can advantageously provide the desired trans configuration in (9) or (D), respectively. Generally the subsequent reaction steps, if any, preserve the trans configuration, which allows for the formation of asenapine and analogues thereof.

The endiester compound of formula (8) may be prepared by ring-opening of the compound (5) or (5a), e.g. by the following scheme:

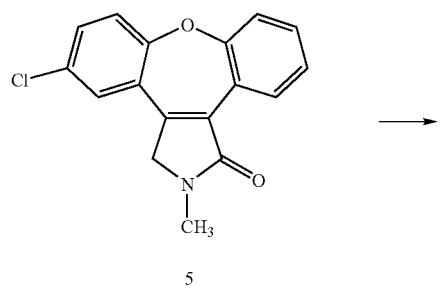

5

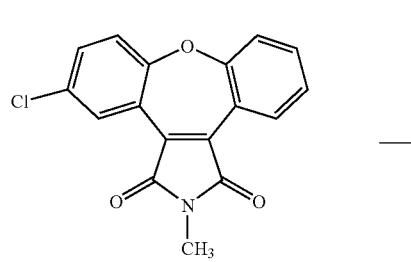

10

-continued

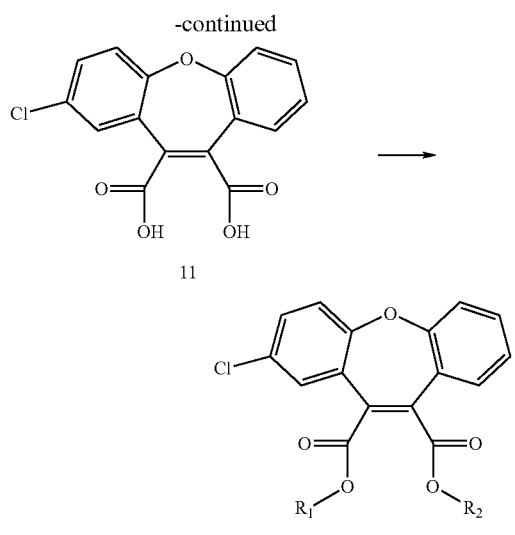

Alternatively, the compound of formula (8) may be produced directly from the acid of the formula (2) or preferably from an ester thereof of formula (2-E), wherein R is preferably C1-C4 alkyl group and most preferably the methyl group, according to the scheme below.

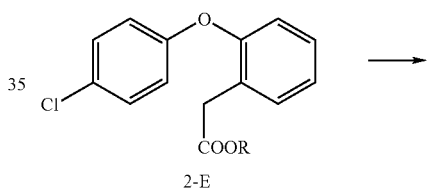

2-E

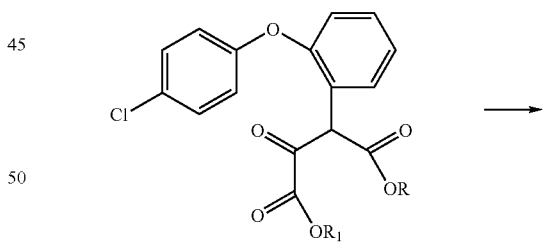

12

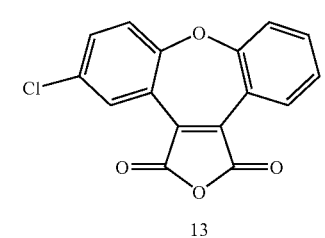

13

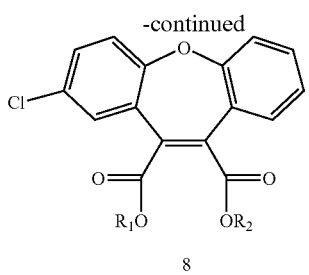

8

Deprotonation of compound (2-E) (e.g. by potassium tert. butoxide) followed by its reaction with di (C1-C4)alkyl oxalate, preferably with dimethyl oxalate, preferably in an organic solvent and conveniently at temperatures close to ambient, provides the desired compound (12) (R, R1 are independently a C1-C4 alkyl group and preferably both are methyl groups) in a good chemical yield. It should be noted that the compound (12) may exist as a mixture of keto- and enol forms.

In further, the compound (12) is converted into the compound of formula (8) by a ring-closure of the oxepine ring. Though this is not strictly necessary, it is nevertheless advantageous first to prepare the anhydride of formula (13) as a reactive intermediate for making the compound (8). The anhydride (13) may be made by reacting the compound (12) with polyphosphoric acid as a solvent and reagent as well, at enhanced temperatures (50–150° C.).

The anhydride compound (13) may provide the desired endiester compound (8) by an esterification. Advantageously, alkylation with an alkyl halide is a suitable way to convert the compound (13) to (8).

The most convenient compound of the general formula (8) is the bis-methyl ester (R1, R2=methyl).

A possible alternative is to start with a regio-isomer of the compound (2)—the acid compound (2a) or an ester thereof of formula (2a-E)—which can provide, under analogical conditions as disclosed above, the compound (12a), which may be converted to the same compound (8).

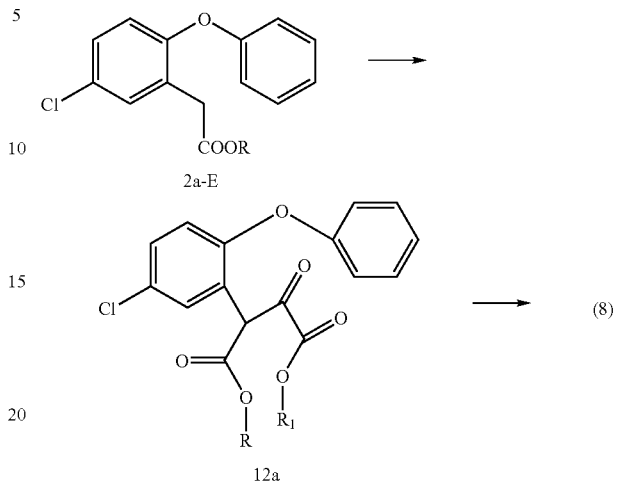

The endiester compound (8) is then selectively or preferentially reduced to compound (9) as mentioned above, which is then converted to asenapine (1) by any suitable route. In one embodiment the conversion involves the following reaction sequence:

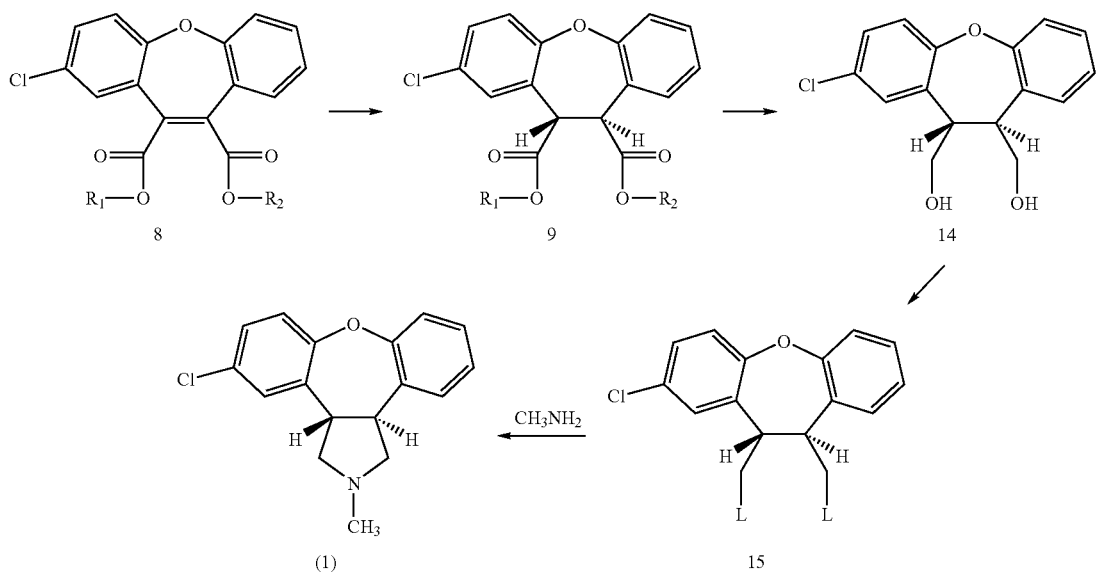

In the first step, the compound (8) is converted into the trans-diester compound (9) by a reduction of the double bond. The reduction of the double bond in the endiester compound (8) runs almost selectively in trans-orientation and it is possible to obtain a product having, in respect to the trans-cis ratio, more than 80%, preferably more than 90% and most preferably even more than 95% isomeric purity. Any convenient reducing agent may be used, for instance magnesium in an alcohol, hydrogen with a hydrogenation catalyst, a hydride reductant, etc.

In a next step, the trans-diester compound (9) is further reduced to a trans-diol (14), whereby the both ester groups are converted into hydroxymethyl groups. Convenient reduction agent comprises a hydride, e.g. lithium aluminum hydride. Advantageously, both reduction processes may be performed within one step.

In a penultimate step, the trans-diol is activated by substitution of the OH-groups by a good leaving group L, for instance by a halogen or by an alkylsulfonyloxy- or an arylsulfonyloxy group. Most convenient group is the mesyloxy group. The so formed activated compound (15) is converted, under very mild conditions, to the desired asenapine by cyclizing the five-membered ring by reaction with methylamine, preferably with aqueous methylamine.

Any of the intermediates of the above process may be isolated from the reaction mixture by conventional methods and purified, if necessary.

The yield of first three steps from compound (8) to compound (15) (L is mesylate group) can be nearly quantitative without necessary purification. The ratio of trans/cis isomers in the compound (9) is often approximately ~95/5.

When R2 contains the appropriate functional groups, the asenapine can be formed by a direct ring formation analogous to the ring closing shown for compound 7 (or 7a) in EP 1710241.

The asenapine produced by the above process may be used as such in pharmaceutical application or may be converted into an acid addition salt. Preferred among the salts is the maleate salt, though any pharmaceutically acceptable acid addition salt is also contemplated.

The invention is further described by way of the following examples, but is not limited thereto.

EXAMPLES

Example 1

Compound (8)

Step 1—Preparation of Compound (12):

Potassium t-butoxide (2.52 g) was suspended in freshly dried diethyl ether (50 ml). Under cooling and while stirring, dimethyl oxalate (3.19 g) was added, followed by addition of the compound (2-E) (R=methyl) (5.0 g) in diethyl ether (10 ml). The mixture was stirred at ~5° C. for 1 hour and then at room temperature for 20 hours. The mixture was poured into ice (100 g) and stirred for 5 minutes. The separated water layer was acidified with 2M HCl to pH 1.5 and extracted with diethyl ether (100 ml). The ether-extract was washed with brine (15 ml), dried and concentrated to give a crude product (12) (5.5 g).

Step 2—Cyclization of (12) to Anhydride (13):

A mixture of compound (12) (15 g) and polyphosphoric acid (120 g, 82% min. as $P_2O_5$) was stirred at 120° C. (oil bath) for 50 minutes and then at 130° C. for 1 hour. After cooling down to room temperature, water (250 ml) was added carefully followed by diethyl ether (200 ml) and ethyl acetate (200 ml). After stirring for 20 minutes, the organic layer was separated and washed with base (1 M NaOH, 2×5 ml). The organic layer was further washed with water (100 ml), brine (100 ml), dried and concentrated in vacuo to give a semi-solid, which was triturated with ether (15 ml) overnight to furnish a yellow solid (13) (1.9 g).

Step 3—Preparation of Dimethylester 8 (R1=R2=methyl):

Anhydride (13) (2.0 g) was suspended in methanol (100 ml). While stirring at room temperature, solid potassium fluoride (500 mg) was added. The mixture was stirred for two hours to give a clear solution. Iodomethane (10 ml) was added and the mixture was further stirred at 60° C. (oil bath) for 24 hours.

After concentration in vacuo, the remaining was redissolved in ethyl acetate (50 ml), washed with NaOH aq. (1 M, 2×10 ml), water (10 ml), brine (10 ml), dried and concentrated in vacuo to give dimethylester (8) (1.81 g).

$^1$H-NMR (400 MHz, $CDCl_3$): 3.89 (s, 6H), 7.19 (m, 2H), 7.23 (dd, $J_1$=1.1 Hz, $J_2$=8.2 Hz, 1H), 7.34 (dd, $J_1$=8.5 Hz, $J_2$=2.6 Hz, 1H), 7.41 (m, 1H), 7.56 (d, J=2.6 Hz, 1H) and 7.59 (dd, $J_1$=7.9 Hz, $J_2$=1.6 Hz, 1H); $^{13}$C-NMR: 52.89, 52.97, 121.05, 122.35, 126.19, 127.85, 129.35, 129.58, 130.53, 131.33, 131.98, 133.35, 137.16, 158.26, 159.75, 166.88 and 167.40.

Example 2

Synthesis of Asenapine (1)

Step 1—Reduction of En-dimethylester (8) to the Dimethyl Ester (9):

A mixture containing 1.1 g (3.2 mmol) of en-dimethylester (8, R1=R2=methyl) and magnesium (0.5 g, ~20 mmol) in a mixture of tetrahydrofuran (5 ml) and methanol (25 ml) was stirred at 60° C. (oil bath) for 1 hour. Magnesium disappeared completely. After the reaction mixture was cooled down to room temperature, acetic acid (2.4 ml) was added and further stirred for 10 minutes.

The mixture was concentrated in vacuo and then re-dissolved in chloroform (50 ml). The organic layer was washed with water (50 ml), brine (25 ml), dried and concentrated to give a desired product (1.1 g). Trans-cis ratio was 97:3 based on HPLC.

Step 2—Reduction of (9) to di-alcohol (14):

To a solution of dimethyl ester (9) from the preceded step (~1.1 g) in pre-dried THF (25 ml), under cooling (ice water) and while stirring, a solution of LiAlH4 (4 ml, 2M in THF) was added in ~20 minutes. After further stirring for 1 hour at room temperature, diethyl ether (50 ml) was added followed by careful addition of water (10 ml) and acidification to pH 4. The separated ethyl ether layer was washed with water (20 ml), brine (20 ml), dried and concentrated to give crude product (14) (1.2 g).

Step 3—Mesylation of (14) to (15):

Under cooling (ice water), to a stirred solution of the diol (14) (425 mg) in dried dichloromethane (10 ml), methanesulphonic acid chloride (430 mg) was added within 1 minute followed by the addition of triethylamine (400 mg) within 1 minute. The resulting mixture was stirred for ~20 minutes at ~5° C. Water (25 ml) was added and the mixture was further stirred for 10 minutes. The separated dichloromethane layer was washed with brine (10 ml), dried and concentrated in vacuo to give a crude solid product (15) (660 mg).

Step 4—Synthesis of Asenapine

A mixture containing di-mesylate (15) (90 mg), acetonitrile (6 ml) and methylamine (0.3 ml, 40% aq.) was sealed in a pressure reactor. The mixture was stirred for 24 hours at 80° C. (oil bath). It was concentrated in vacuo and re-dissolved in dichloromethane (25 ml). After washing with water (25 ml), brine (10 ml), the organic layer was dried and concentrated in vacuo to give the desired product asenapine (60 mg). Both NMR and HPLC showed that the contamination of cis-isomer of Asenapine was less than 2%. Analytical sample was obtained by chromatography. $^1$H-NMR (400 MHz, $CDCl_3$): 3.06 (s, 3H), 3.65-3.76 (m, 2H), 3.86-3.97 (m, 4H), 7.01-7.33 (m, 7H).

Each of the patents, patent applications, and journal articles mentioned above are incorporated herein by reference. The invention having been described it will be obvious that the same may be varied in many ways and all such modifications are contemplated as being within the scope of the invention as defined by the following claims.

We claim:

1. A process, which comprises reducing a compound of formula (C) to preferentially form a trans isomer compound of formula (D)

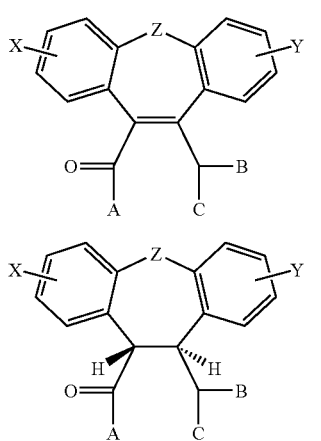

wherein Z represents an oxygen, sulfur, or methylene linkage group;

X and Y independently represent hydrogen, an alkyl group, a hydroxy group, an alkoxy group, a halo group, a nitro group, an amino group, a substituted amino group, a cyano group, a sulfonyl group, a carboxyl group, a substituted carboxy group and combinations thereof, and wherein X and Y can each be present up to four times on their respective rings and each occurrence is independently selected;

A represents a group of the formula O—R1;

B represents hydrogen or a ═O group; and

C represents an amino group, a methylamino group or a group of the formula O—R2; wherein R1 and R2 are each individually selected from hydrogen, alkyl, alkynyl and aralkyl groups.

2. The process according to claim 1, which further comprises converting said compound of formula (D) to a ring-closed compound of formula (B)

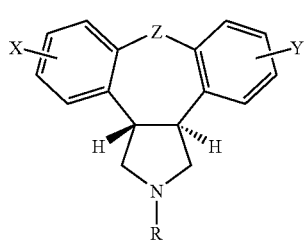

wherein R represents an alkyl or an aralkyl group.

3. The process according to claim 2, wherein said compound of formula B is asenapine.

4. A process, which comprises reducing a compound of formula (8) to preferentially form a trans ester of formula (9)

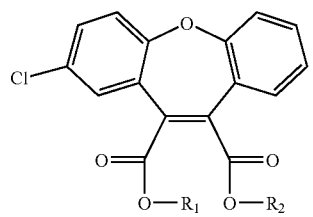

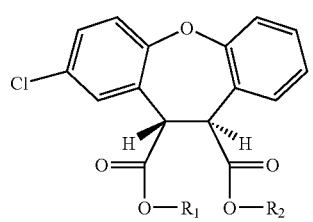

wherein R1 and R2 are the same or different and represent an alkyl, alkynyl or aralkyl group.

5. The process according to claim 4, wherein R1 and R2 represent the same C1-C4 alkyl group.

6. The process according to claim 5, wherein R1 and R2 each represent a methyl group.

7. The process according to claim 4, wherein said reduction step is carried out with a reducing agent selected from the group consisting of (i) magnesium in an alcohol, (ii) hydrogen with a hydrogenation catalyst, and (iii) a hydride reductant.

8. The process according to claim 4, wherein said preferential reduction of said compound of formula (8) produces said trans isomer compound of formula (9) in an isomeric purity of at least 70%.

9. The process according to claim 4, wherein R1 and R2 each represent a methyl group and said preferential reduction of said compound of formula (8) produces said trans isomer compound of formula (9) in an isomeric purity of at least 80%.

10. The process according to claim 4, which further comprises converting said compound of formula (9) to asenapine of formula (1)

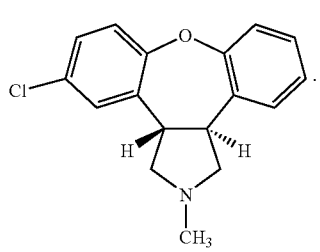

11. The process according to claim 10, wherein said conversion comprises:

(i) converting the ester groups in the compound of formula (9) into hydroxymethyl groups yielding the compound of formula (14);

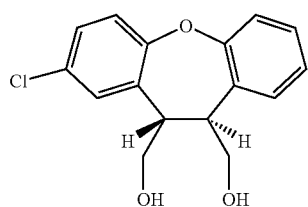

14

(ii) converting the compound (14) into compound (15)

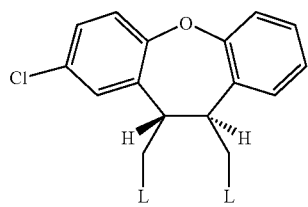

15 wherein L represents a leaving group selected from a group consisting of a halogen, an alkylsulfonyloxy or an arylsulfonyloxy group; and (iii) reacting methylamine with the compound (15) to yield the compound (1).

12. The process according to claim 11, which further comprises converting the compound of formula (1) into a pharmaceutically acceptable salt.

13. The process according to claim 11, wherein the isomeric purity of each of the compounds of formulae (9), (14), (15) and (1) is at least 90%.

14. The process according to claim 13, wherein R1 and R2 in formulae (8) and (9) represent a methyl group; and L in formula (15) represents a mesyloxy group.

15. The process according to claim 4, which further comprises forming said compound of formula (8) by a method which comprises:

a) converting a compound of formula (2-E) to a compound of formula (12)

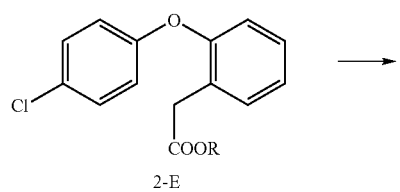

2-E

-continued

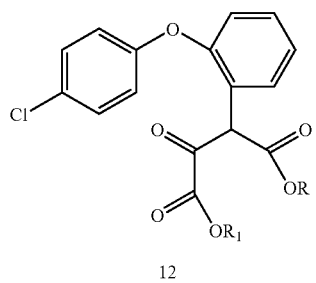

12 wherein R and R1 each independently represent a C1-C4 alkyl group by a reaction of (2-E) with a dialkyl oxalate; and b) converting the compound (12) into said compound of formula (8).

16. The process according to claim 15, wherein the step b) comprises:

(b1) converting the compound (12) into a compound of formula (13);

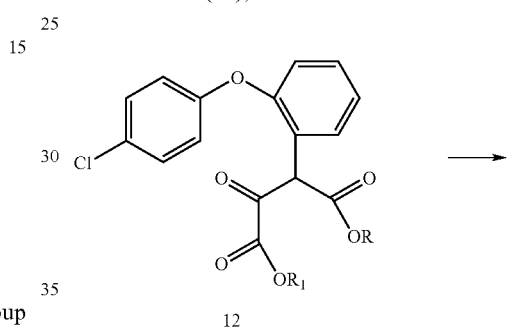

12

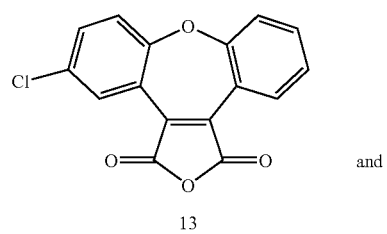

13 and (b2) ring opening the anhydride ring in the compound (13) with an alkylation agent, to form said compound of formula (8).

17. A compound of formulae (8), (9), (14) or (15)

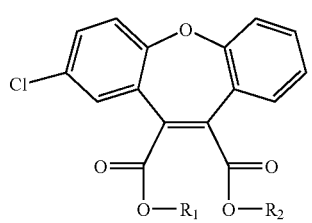

8

-continued

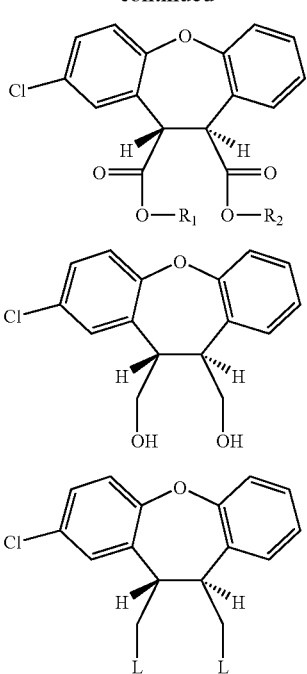

wherein R1 and R2 are the same or different and represent an alkyl, alkynyl or aralkyl group; and L represents a leaving group selected from a group consisting of a halogen, an alkylsulfonyloxy or an arylsulfonyloxy group.

18. The compound according to claim 17, wherein R1 and R2 represent a methyl group and L represents a mesyloxy group.

19. The compound according to claim 17, wherein said compound is a compound of formula (9), (14) or (15) and having a trans isomeric purity of at least 80%.

20. The compound according to claim 18, wherein said compound is a compound of formula (9), (14) or (15) and having a trans isomeric purity of at least 80%.

21. The process according to claim 1, wherein said reduction step is carried out with magnesium in an alcohol.

22. The process according to claim 7, wherein said reducing agent is magnesium in an alcohol.

* * * * *